US008825165B2

(12) United States Patent
Possover (10) Patent No.: US 8,825,165 B2
(45) Date of Patent: *Sep. 2, 2014

(54) LAPAROSCOPIC TRANSPELVEO-ABDOMINAL IMPLANTATION OF MULTIPLE CHANNEL ELECTRODES TO THE ENDOPELVIC PORTIONS OF THE PUDENDUS AND SCIATIC NERVES

(76) Inventor: Marc Possover, Hagendorn (CH)

( * ) Notice: Subject to any disclaimer, the term of this patent is extended or adjusted under 35 U.S.C. 154(b) by 406 days.

This patent is subject to a terminal disclaimer.

(21) Appl. No.: 13/101,252

(22) Filed: May 5, 2011

(65) Prior Publication Data

US 2011/0276055 A1    Nov. 10, 2011

Related U.S. Application Data

(63) Continuation-in-part of application No. 12/626,274, filed on Nov. 25, 2009, now Pat. No. 8,489,191, which is a continuation-in-part of application No. 11/708,209, filed on Feb. 20, 2007, now Pat. No. 8,019,423.

(60) Provisional application No. 61/331,579, filed on May 5, 2010.

(51) Int. Cl.
*A61N 1/36* (2006.01)

(52) U.S. Cl.
CPC ........ *A61N 1/36007* (2013.01); *A61N 1/36107* (2013.01)

USPC .................. 607/41; 607/1; 607/115; 606/129

(58) Field of Classification Search
USPC .......... 606/32–35, 41, 42, 129; 607/2, 39–41, 607/46, 48, 49
See application file for complete search history.

(56) References Cited

U.S. PATENT DOCUMENTS

| 6,990,376 B2 * | 1/2006 | Tanagho et al. ................. 607/40 |
| 7,328,068 B2 * | 2/2008 | Spinelli et al. ................. 607/39 |
| 8,019,423 B2 * | 9/2011 | Possover ......................... 607/40 |
| 8,489,191 B2 * | 7/2013 | Possover ......................... 607/41 |
| 2006/0122660 A1 * | 6/2006 | Boveja et al. ................... 607/40 |
| 2007/0198065 A1 * | 8/2007 | Possover ......................... 607/40 |
| 2010/0145409 A1 * | 6/2010 | Possover ......................... 607/41 |
| 2013/0023949 A1 * | 1/2013 | Possover ......................... 607/39 |

OTHER PUBLICATIONS

Affidavit filed Mar. 14, 2011 by Dr. Marc Possover in U.S. Appl. No. 11/708,209.*

* cited by examiner

*Primary Examiner* — Kathleen Holwerda
(74) *Attorney, Agent, or Firm* — Bachman & LaPointe, P.C.

(57) ABSTRACT

A method for altering operation of a nerve related to a given body condition includes the steps of: laparascopically gaining access to the endopelvic area of the abdomen through the abdominal wall; implanting a multiple channel electrode through the access on endopelvic portions of at least one nerve of the sciatic nerve, the pudendus nerve, or both; and operating the electrode to electrostimulate the at least one nerve.

9 Claims, 7 Drawing Sheets

LAPAROSCOPIC TRANSPELVEO-ABDOMINAL IMPLANTATION OF MULTIPLE CHANNEL ELECTRODES TO THE ENDOPELVIC PORTIONS OF THE PUDENDUS AND SCIATIC NERVES

CROSS REFERENCE TO RELATED APPLICATION

This application claims the benefit of the filing date of provisional application 61/331,579, which was filed on May 5, 2010. This application is also a continuation-in-part of U.S. patent application Ser. No. 12/626,274 filed Nov. 25, 2009, now U.S. Pat. No. 8,489,191 which is a continuation-in-part of U.S. patent application Ser. No. 11/708,209 filed Feb. 20, 2007, now U.S. Pat. No. 8,019,423.

FIELD OF THE INVENTION

The invention is based on the feasibility of laparoscopic/endoscopic implantation (LION procedure—Laparoscopic Implantation Of Neuroprothesis) of multiple channel electrodes to the endopelvic portions of the sciatic and pudendal nerves (supralevator portions) by pelveo-abdominal approach (transperitoneally/retroperitoneally) for neuromodulation/stimulation of the pudendal and sciatic nerves together or separately in different combinations, or parts of the sciatic nerve (gluteal nerves, afferent and efferents sciatic fascicules) and/or of the pudendal nerve (afferent and efferent fascicules) in different combinations. The invention is indicated for treatment for neurogenic and non-neurogenic troubles or loss of function and pain in the lower extremities and/or pelvic and perineal organs and/or perineum.

BACKGROUND OF THE INVENTION

Several techniques for stimulation of the pelvic nerves have been developed in the past.

The sacral nerve root stimulation with sacral deafferentation, also called Brindley bladder controller, is based on the implantation of electrodes to the sacral nerve roots directly at their emergence from the spinal cord. This procedure requires a dorsal surgery with laminectomy, meaning exposure of the nerves at the back after opening the rachis. This procedure allows only en bloc stimulation of the sacral nerve roots, which means stimulation of the nerve fibers passing through the roots destined to the pelvic organs, the sphincter and the lower extremities all together and not separately. Therefore, stimulation induces at the same time bladder contraction, rectum contraction, erection and motion in the lower extremities. For control of bladder hyperactivity in spinal cord injured people, this technique required the cutting of the dorsal branches of the sacral nerves roots (sacral deafferentation) and post-stimulus effect for induction of a non-physiologic bladder voiding (bladder voiding occurs not during stimulation of the nerves but after interruption of the stimulation; early relaxation of the sphincters with further contraction of the bladder for a few seconds permits passing urine through the urethra). Therefore the stimulation must be repeated several times before the bladder is empty.

Transforaminal sacral nerve stimulation (Tanagho—U.S. Pat. No. 4,607,639, FIG. 1), is a technique wherein a multiple channel electrode is introduced by blind percutaneous puncture from the back through the sacral foramen to the sacral nerve roots. Therefore, one electrode permits stimulation of only one sacral nerve root. That means that for the stimulation of the entire nerves destined to the lower limbs and the pelvic organs and sphincters, five electrodes would be necessary (there are five sacral nerves roots per side). That is not feasible since all actual pacemakers have one or at most two channels. In this technique, stimulation cannot permit selective stimulation of the nerve fibers destined to the lower limbs, to the pelvic organs and to the sphincter—similarly to the Brindley implantation.

The perineal technique of implantation is a technique wherein an electrode is placed to the extrapelvic, that is, the perineal or infralevator portion of the pudendal nerve or its branches by perineal implantation at the space between the rectum and vagina in a female or testicles in males, the vagina or the rectum. In other words, this is an approach from below, between the legs. This technique of implantation permits selective stimulation of the pudendus nerve and its branches but permits a stimulation neither of the sciatic nerves, nor of the sacral nerves roots nor of the endopelvic portion of the pudenda nerve nor of any endopelvic nerves, because the perineum is separated from the pelvis (supralevator) by the pelvic floor.

SUMMARY OF THE INVENTION

None of these previous techniques permit a selective implantation of electrodes to all endopelvic nerves. Only the approach of the nerves by passing through the abdomen and pelvis permits this. Only the laparoscopic pelveo-abdominal approach (transperitoneal or retroperitoneal) offer a visual access to all endopelvic nerves and plexuses and in the same time implantation of an electrode, and a morphologic and functional exploration de visu of the nerves. This is of importance because it can permit to exclude and eventually treat pathologies of the nerves such as fibrosis, endometriosis or a vascular entrapment before decision of implanting an electrode.

The present invention therefore provides a method for altering operation of a nerve related to a given body condition, comprising the steps of: laparascopically gaining access to the endopelvic area of the abdomen through the abdominal wall; implanting a multiple channel electrode through the access on endopelvic portions of at least one nerve of the sciatic nerve, the pudendus nerve, or both; and operating the electrode to electrostimulate the at least one nerve.

Implanting a multiple channel electrode on the pudendal nerve allows for treatment of body conditions selected from the group consisting of urinary and fecal incontinence; bladder, rectum and genital hyperactivity; bladder/rectum retention; erection disfunction; pain and combinations thereof.

Implanting of a multiple channel electrode on the sciatic nerve allows for treatment of spasticity and spasms of the lower extremities, pain, osteoporosis, decubitus lesions, spinal cord injuries and combinations thereof.

Implanting of the multiple channel electrode on both the sciatic and pudendus nerves allows for stimulation of combinations of both nerves which is particularly useful in spinal cord injury situations.

BRIEF DESCRIPTION OF THE DRAWINGS

A detailed description of preferred embodiments of the present invention follows, with reference to the attached drawings wherein.

DETAILED DESCRIPTION

The invention relates to a method for implanting a multiple channel electrode onto specific nerves and nerve roots in the endopelvic region, and thereby to address a number of issues as will be discussed below.

Figure 1:
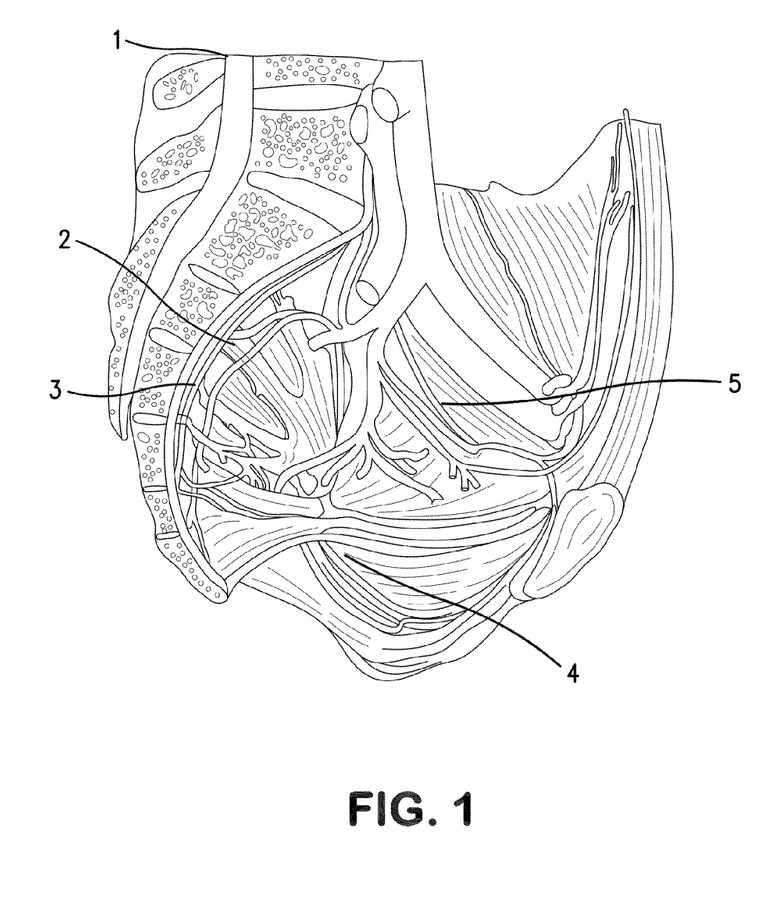
FIG. 1 illustrates the approach and implantation area in accordance with the present invention as well as the approach and implantation area of several known methods.

FIG. 1 is an illustration of the human pelvis and shows approaches and implantation areas of various prior art methods as well as the method disclosed herein.

Referring to FIG. 1, from the upper left portion of the figure, the "Brindley" surgical approach or "dorsal spinal approach" is shown at arrow 1. Next on the left of the figure, a percutaneous tranforaminal approach such as is disclosed by Tanagho is shown at 2. The area in which implantation is made under the Tanagho approach is shown at 3. In the lower area of the figure, implantation area and perineal/vaginal approach are shown at reference 4, and this corresponds to the teachings of Mann.

The implantation area of the present invention is the endopelvic region, and this region is accessed in accordance with the present invention through laparoscopic entry via access through the abdominal wall. The region 5 which can be reached in this manner is shown in FIG. 1. In this region 5, a collection of highly important nerves can be accessed together, and multiple channel electrodes can be implanted on these nerves to address a number of problems which have been long-standing issues in this art.

Figure 2:
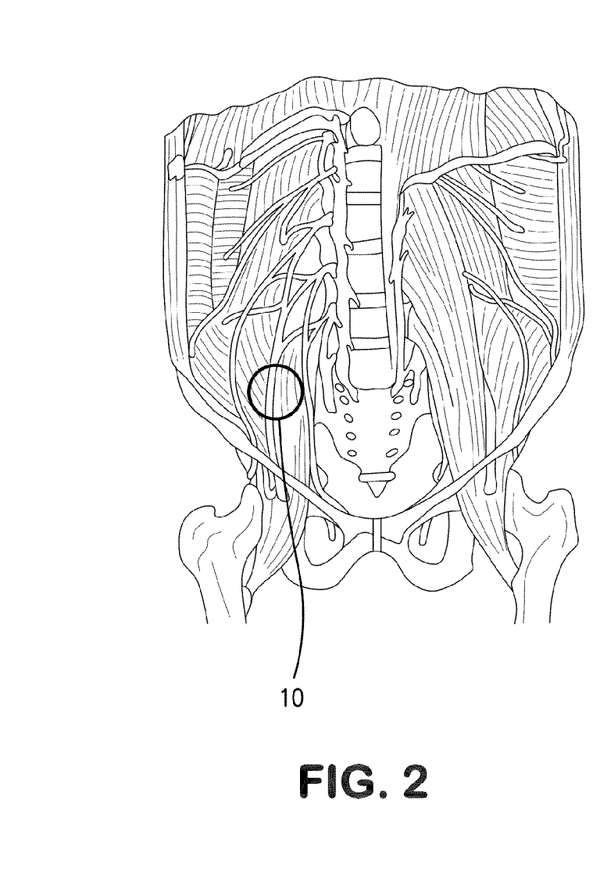
FIG. 2 illustrates the location of the femoral nerve.
Figure 3:
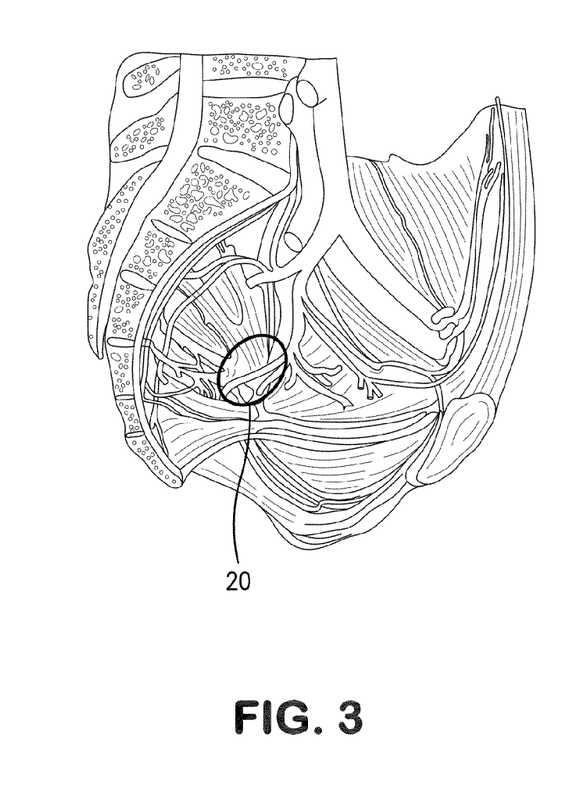
FIG. 3 illustrates the location of the sciatic and pudendus nerves.

The electrodes are placed to the endopelvic portions of the pelvic nerves. The exact location of such nerve is as is shown in FIG. 2, showing the femoral nerve 10, and FIG. 3 shows the location 20 of the sciatic and pudendus nerves.

For the sciatic nerve, the endopelvic portion of the sciatic nerve is directly after fusion of the different sacral nerves roots and just before the sciatic nerve disappears through the greater sciatic foramen. At this point, a multiple channel electrode can be placed as shown in FIG. 3, and this permits global pudendus and sciatic stimulation, but also selective stimulation of the sciatic nerve, of different portions of the sciatic nerves or of the pudendus nerve but also selective stimulation of the inferior and superior gluteal nerves.

For the pudendus nerve, the endopelvic portion of the pudendus nerve (supralevator portion) is directly after it emerges out of the sacral plexus and just before it leave the pelvis through the lesser sciatic foramen.

For the femoral nerve, the endopelvic retroperitoneal portion of the femoral nerve is lateral to the major psoas muscle before it leaves the abdominal cavity through the inguinal canal.

For the laparoscopic approach, a transperitoneal or retroperitoneal approach is used, while the introduction of the trocars is done through the abdominal wall (ideally at the navel) or in other places such as the pelvic wall. Further endoscopic ways can be used, such as LESS, NOTES, transgastric, transrectal, transvaginal, transvesical, and the like, but the laparascopic approach through the abdominal wall is preferred.

For exposure of the endopelvic portion of the sciatic and pudendal nerves, three ways of dissection can be used, one through the lumbosacral fosse, the second through the obturatoric fosse and the third through the retropubic space (Retzius space).

The functional integrity of the nerves is obtained by intraoperative electrical stimulation, a technique which is known to those skilled in the art.

A multiple channel electrode is preferably implanted in direct contact to both the sciatic and the pudendal nerves in area 20 as shown in FIG. 3. The implantation can be done uni- or bilaterally (depending from the indication) while the cable(s) of the electrode(s) are tunneled retroperitoneally and connected to a permanent rechargeable generator implanted subcutaneously or endopelvically or endoabdominally or in direct connection to the electrode ("intelligent electrode").

Figure 4:
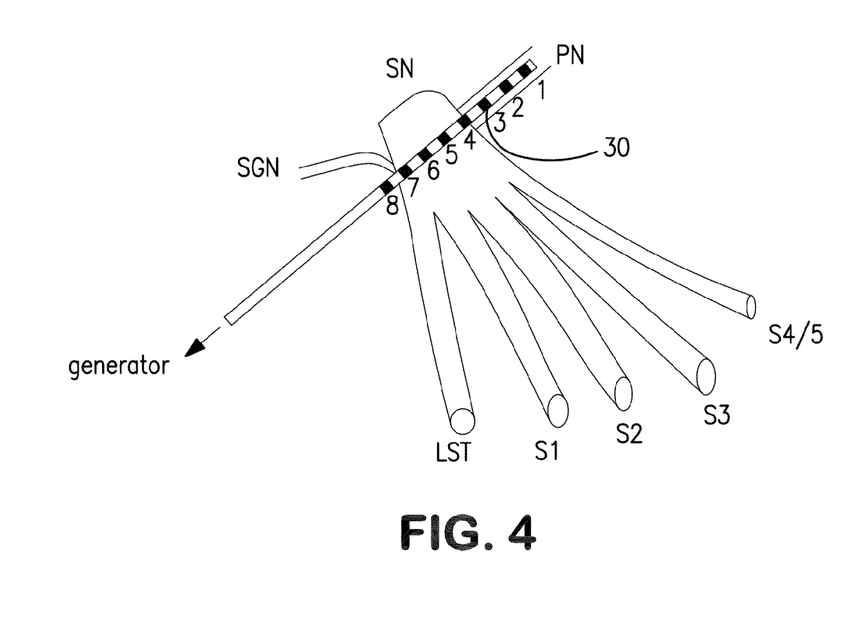
FIG. 4 illustrates positioning of a multi-pole electrode in accordance with the present invention.

The pudendus nerve is the nerve of the sphincters that control the contraction/relaxation of the anal and urethral sphincters but also genital organs. Selective pudendal stimulation (continuous or discontinuous) is obtained by application of a current on the part of the electrode 30 (FIG. 4) that is in direct contact with the pudendal nerve (poles 1, 2 and 3 in FIG. 4).

Pudendal stimulation can be indicated in different pathological situations, including urinary and fecal incontinence, bladder, rectum and genital hyperactivity, bladder/rectum retention, trouble with erections, pain control and others, each of which is further described below.

For urinary and fecal incontinence, stimulation of the pudendus nerve (FIG. 4) induces contraction and therefore closure of the anal and urethral sphincters and can be indicated:

in pathologies of the sphincters themselves (myogenic etiologies);

secondary to surgeries (radical prostatectomy, hysterectomy, episiotomy, anal surgery, delivery, radiotherapy, local tumors, infectious diseases and abscess, fistula, malformations, prolaps;

in pathologies of the innervation of the sphincters (neurogenic etiologies); and spina bifida, cauda equina, lesions of pelvic nerves secondary to surgery, radiotherapy, delivery, pelvic traumas, infections of the peripheral nervous system, pathologies of the central nervous system (Parkinson syndrome, dementia, infections, diseases, tumor, Strock).

Figure 5:
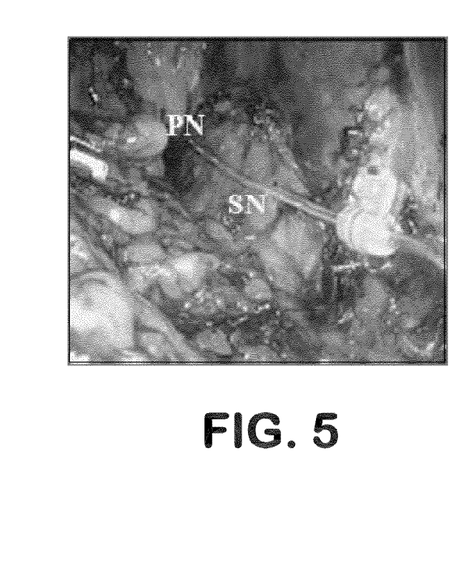
FIG. 5 is a photograph illustrating the placement of a multi-pole electrode in accordance with the invention.

Bladder, rectum and genital hyperactivity can be addressed with stimulation of the pudendus nerve which can also induce an inhibition of detrusor and rectum contraction (See FIG. 5) and can be indicated in bladder over-activity (non-neurogenic)—neurogenic bladder hyperactivity (spina bifida, spinal cord injuries, para- and tetraplegics, multiple sclerosis, pathologies of the pelvic nerves (radiation, surgeries, delivery, tumor, endometriosis), pathologies of the central nervous system (dementia, Parkinson syndromes, Infections of nervous system, Strock)—secondary lesions of the spinal cord (spinal cord injuries, tumor, infection)—interstitial cystitis—mono- and polyneuropathies (autoimmune, endometriosis, diabetes)—neurogenic cystopathies (diabetes), and pathologies and lesions (secondary to surgery, vaginal delivery). FIG. 5 is a photographic image showing a multiple channel electrode implanted on the pudendus nerve (PN) and the sciatic nerve (SN).

Figure 6:
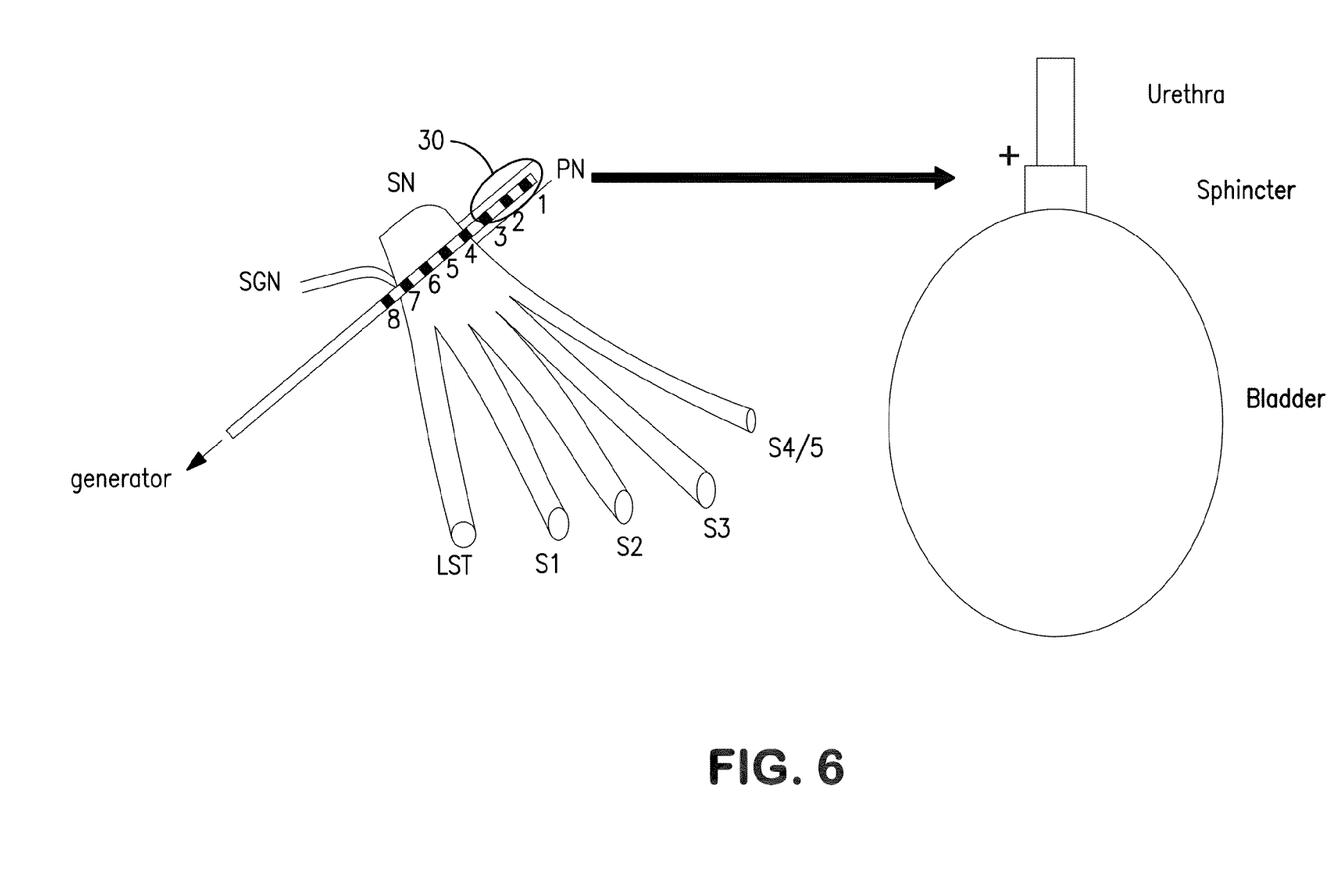
FIG. 6 illustrates a further embodiment of the present invention utilizing a multi-pole electrode.
Figure 7:
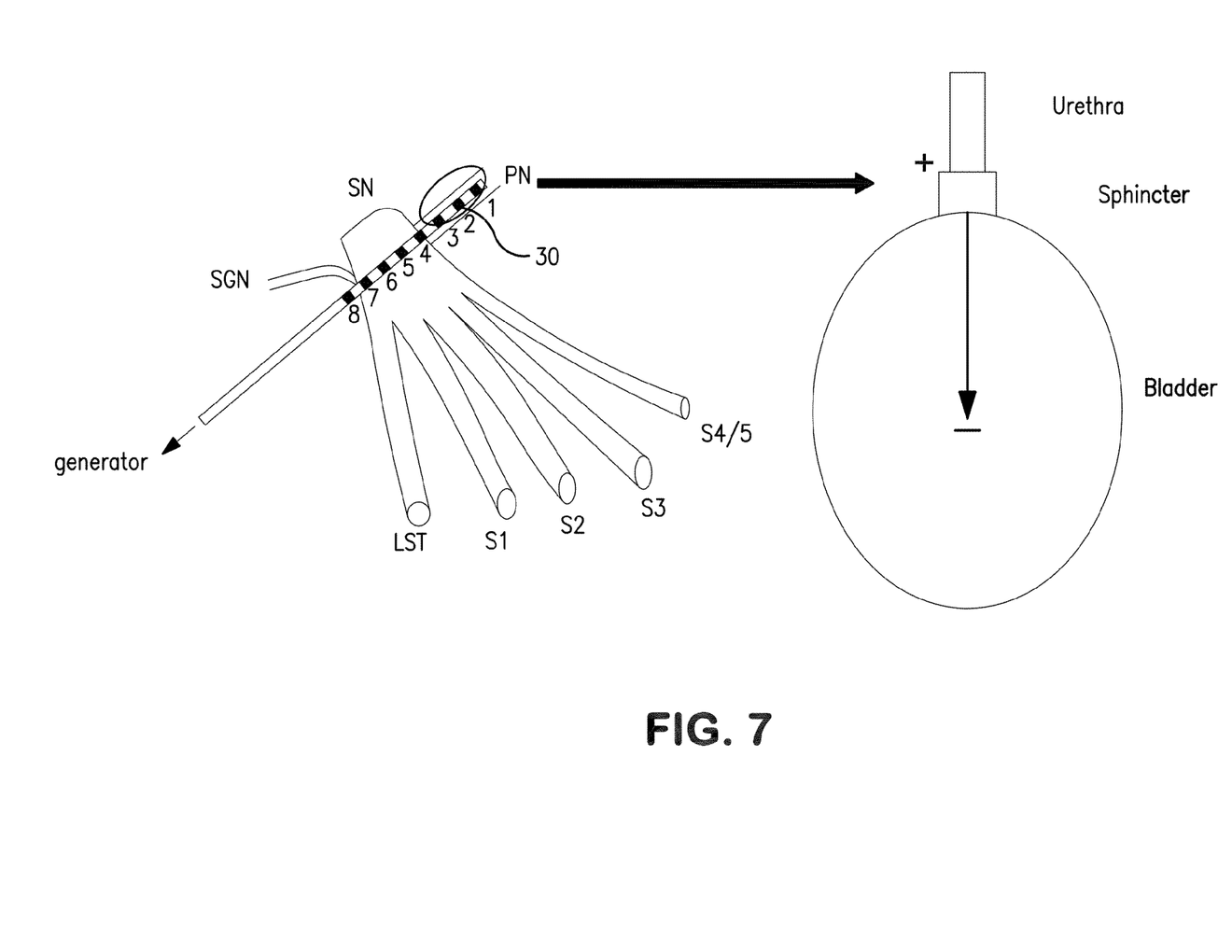
FIG. 7 still further illustrates the embodiment of FIG. 6.
Figure 8:
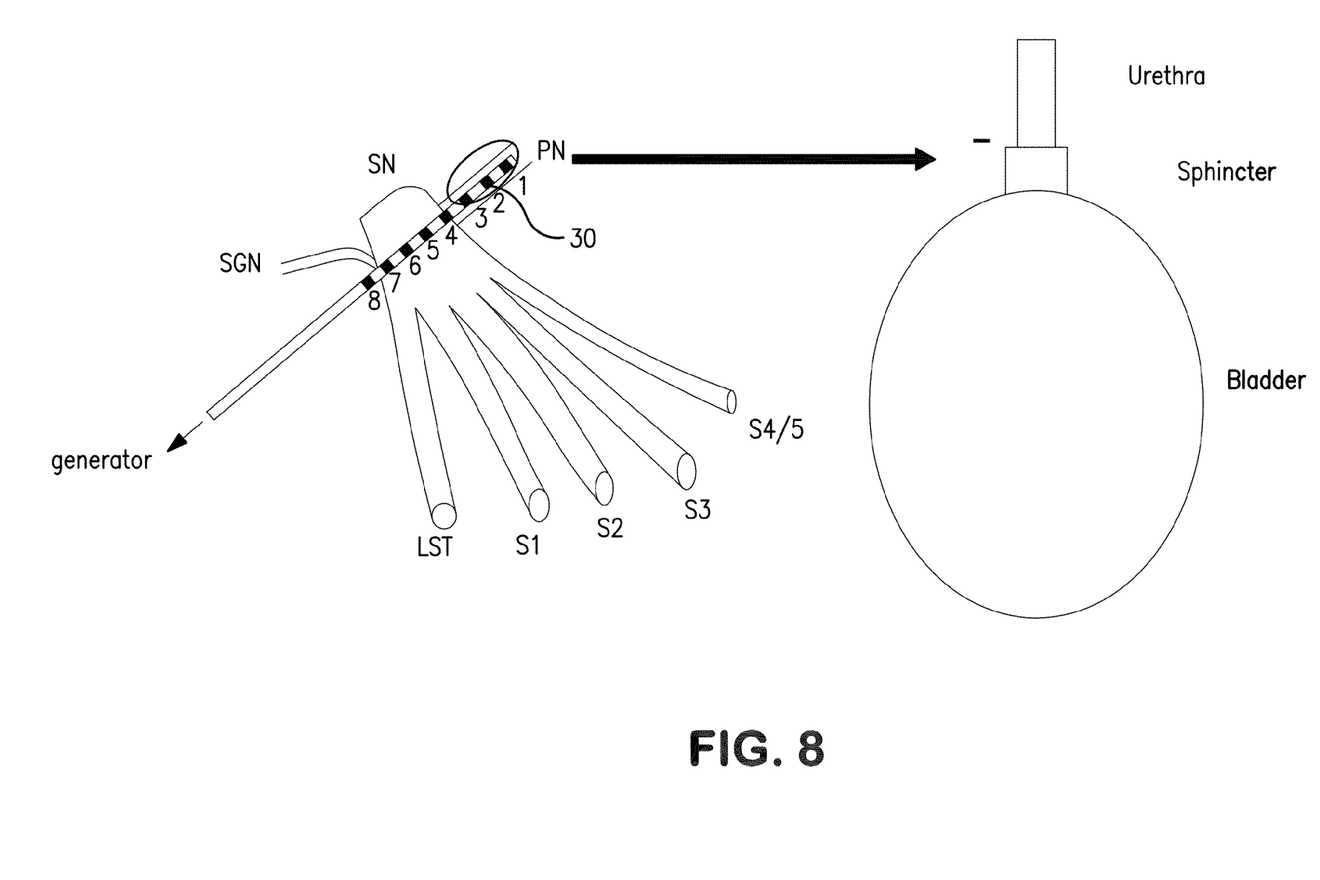
FIG. 8 still further illustrates the embodiment of FIG. 6.
Figures 9, 10:
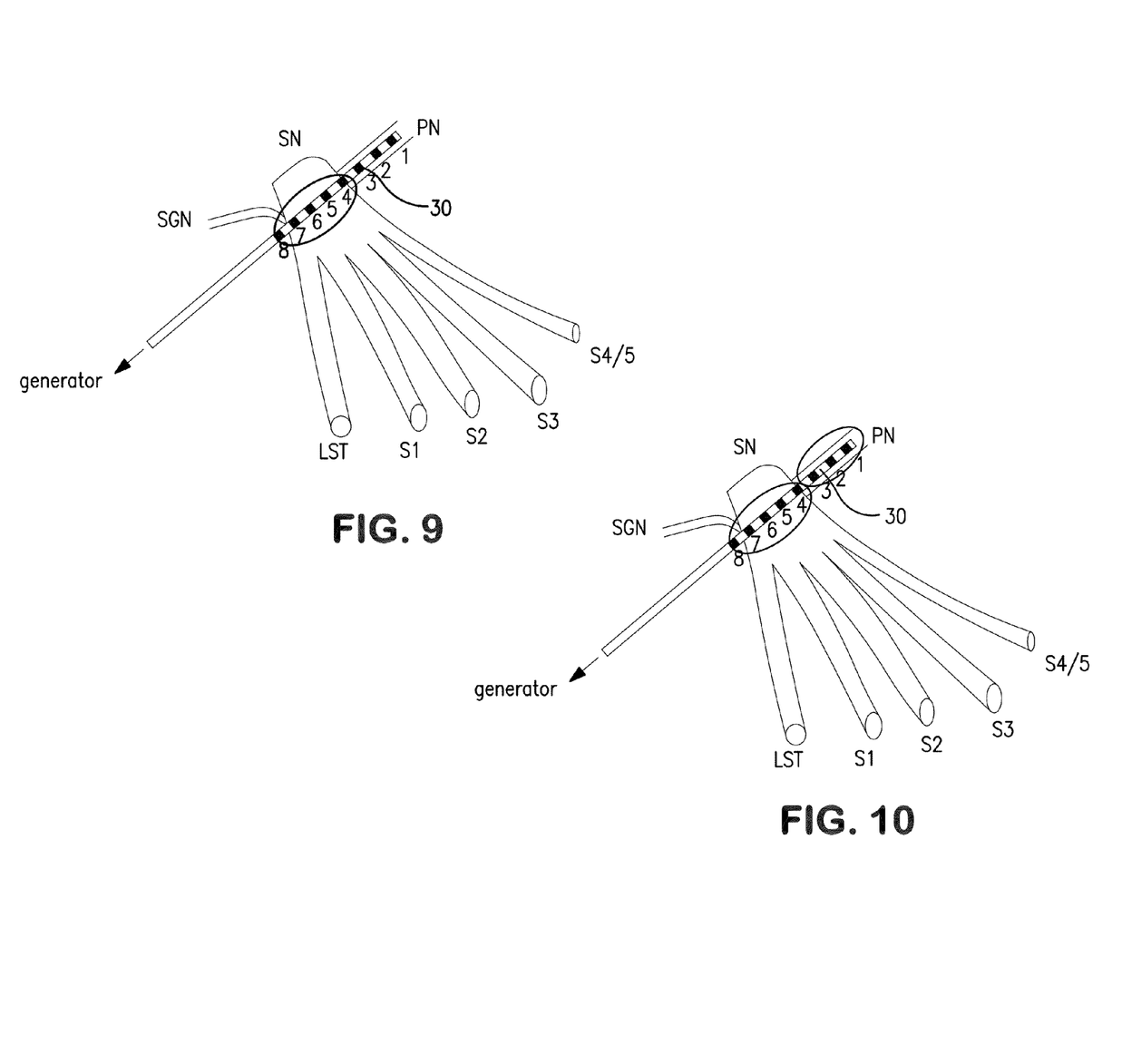
FIGS. 9 and 10 further illustrate placement of a multi-pole electrode in accordance with the present invention

Bladder/rectum retention (detrusor Hypo- or atonia), Detrusor-Sphincter-Dyssynergy can be addressed with stimulation of the pudendus nerve as well. In bladder hypo- or atonia, the detrusor is not able to develop enough intravesical pressure to permit urine to pass the urethral sphincter. In Detrusor-Sphincter-Dyssynergy (DSD), the contraction of the urethra and the bladder is not coordinated so that when the bladder contracts, the sphincter, instead of relaxing, contracts too and blocks the passage of urine. In such situations, blockade of the sphincters in opened status permits passage of urine or stool (FIG. 6). Such a pudendus nerve blockade can be obtained by three different kind of stimulation, namely high-frequency pudendus-nerve-conduction-blockade (Kilgore K L, Bhadra N. Nerve conduction block utilizing high-frequency alternating current. Med Biol Eng Comput 2004; 42: 394-406); anode blockade; and noise (H C. Tuckwell, J. Jost. Inhibition and modulation of rhythmic neuronal spiking by noise. Physical Review E, 2009, 80, 031907).

Trouble with erection or erection disfunction can also be addressed. The pudendal nerve is involved in erection. Therefore, the LION procedure for recovery or improvement of erection can be indicated in myogenic, psychogenic, neurogenic and non-neurogenic indications. A further indication is functional troubles of the vaginal function in women (vaginismus, vaginal spasms).

For pain control, because pudendal afferents fibers also transport sensitive and pain information to the central nervous system, pudendal stimulation can also be used for treatment for pain, such as pudendal pain, rectal/vaginal/perineal pain, cystodyny, prostadyny, pelvic pain syndrome, dyspareuny, and vulvodyny.

The sciatic is the nerve destined to the buttock and the entire dorsal aspect of the lower extremities. It is the nerve for standing up and stabilization of the pelvis, but also for motion of the feet (flexion/extension). All sciatic fibers are only located together inside the pelvis, where electrodes are placed according to the invention. Selective sciatic stimulation (continuous or discontinuous) is obtained by application of current to the part of the electrode that is in direct contact with the sciatic nerve (poles 4, 5, 6, 7, 8—FIG. 4). Because several poles are in direct contact to the sciatic nerve, stimulation can be applied to the entire nerve or to different parts (gluteal nerves) of the nerve.

Therefore sciatic stimulation can be indicated in different pathological situations examples of which include spasticity and spasms of the lower extremities, decubitus lesions, pain control, spinal cord injuries and the like.

Stimulation of the sciatic nerve permits control of spasticity and spasms in the lower limbs (eventually in combination with femoral nerve stimulation) because of neuromodulation of the afferent fibers contained in the sciatic nerve. In comparison to other kinds of blockade of the spasticity (sacral deaferrentiation, muscular botulinum injections, Baclofene pump) that all induce a muscle atrophy (myoatrophy), the blockade of spasticity using sciatic nerve neuromodulation induces a muscle training and therefore increase of muscle mass of the legs. This technique can be indicated in following conditions: spina bifida, spinal cord injuries, para- and tetraplegics, multiple sclerosis, pathologies central nervous system (dementia, Parkinson syndromes, infectious diseases of nervous system, Strock)—secondary lesions of the spinal cord (tumor, infectious diseases)—mono- and polyneuropathies (autoimmune, diabetes).

Stimulation of the sciatic nerve permits control of all pain from the buttocks and lower extremities passing through the sciatic nerve itself.

Stump and phantom pain secondary to amputation or other surgeries, poly-mono-neuropathy, Sudeck Morbus, secondary lesions and pathologies of the sciatic nerves and its branches (tumor, infection, surgical or traumatic lesions can also be addressed)

In the present invention, a multiple channel electrode can be placed in direct contact to the sciatic and pudendal nerves together. Selective stimulation of one or the other is feasible as described previously, but in pathologies involving both nerves, stimulation of both nerves in different combinations can be helpful. For example, in patients affected by multiple sclerosis, stimulation of both nerves can permit at the same time control of pain (pudenda pain, leg pain), spasticity of the lower extremities, bladder hyperactivity, incontinence and retentions. In spinal cord injured patients and spina bifida, the LION (laparoscopic implantation of neuroprothesis) procedure to the pudendal and sciatic nerves together permit to control not only dysfunction but also to recover function as described below.

Spinal cord injuries (para- and tetraplegics) are at an area of application for the invention. Bladder overactivity (BO) that occurs as a consequence of pathologies of the central or peripheral nerve system may cause incontinence, and when this occurs with detrusor external sphincter dyssynergia (DSD), high bladder pressures with vesico-ureteric reflux can also occur. Self-catheterization is a simple and efficient method of voiding the bladder, but maintaining low-pressure normally requires the use of medical treatment or botulinum therapy. A complete biological cure for spinal cord injury is, according to the literature, unlikely to be developed in the near future, and therefore electrical devices are still required to restore control of the lower urinary and gastrointestinal tracts. The Finetech-Brindley bladder controller is at present considered the only clinically available implantable system for bladder control, but is usually accompanied by a dorsal rhizotomy which is sufficient for a large number of paralyzed patients to reject the procedure since it is irreversible and may abolish sexual and defecation reflexes. Other electrical stimulation techniques currently under investigation also show promise but until now, no clinical device can be said to have solved the problem of bladder control as low-pressure physiological voiding cannot be reproduced yet and no device has successfully incorporated methods to produce both voiding and suppression of neurogenic detrusor overactivity in SCI people.

Since laparoscopy permits implantation of electrodes to the sciatic nerves, the pudendal nerves and the sacral nerves roots, laparoscopic approach to the endopelvic nerves permit new strategies of electrical stimulation of the pelvic nerves to enhance pelvic organs and lower extremity functions. The LION procedure is the only method that enables recovery of pelvic functions and functions of the lower extremities in spinal cord injured people, and spina bifida.

Other research had been involved in the field of recovering locomotion in spinal cord injured patients. Some of them concentrate on implantation of electrodes to the muscles themselves, in direct contact or through the skin. Epimysial electrodes (electrodes directly placed on the muscles) showed the disadvantage that because on contraction of the muscles, strong fibrosis developed between the electrode and the muscle that inhibited, over time, the transmission of the current from the electrode to the muscles. A further problem was the breakage of cable of the electrode which passed under the skin.

Other research focused on the placement of electrode to the nerves involved in locomotion but outside the pelvis. These techniques also had the problems of cable breakages and dislocation of electrodes. The LION procedure permits implantation of electrodes to all pelvic nerves in safe position deeply into the pelvis and in the protection of the pelvic bone where no movement occurs, and there is less risk of dislocation and cable breakage.

In spinal cord injured people, both pudendal and sciatic stimulation in different combination and different currents are required. FIGS. 7-10 show application of different currents and different combinations which can be used according to the invention to address a number of issues in spinal cord injury situations.

Inhibition of hyperactivity of the bladder and of the rectum is obtained by unilateral or bilateral selective pudendal stimulation (continuous or discontinuous).

Blockade of bladder hyperactivity can be obtained in different ways. Sacral deafferentation (dorsal rhizotomy) permits elimination of detrusor hyperreflexia and DSD. However the loss of reflex erection and defecation and also the fact of "cutting nerves" are sufficient for a large number of patients to reject the procedure. Several medicaments (muscarinic, anticholinergic) do exist but many patients stop these therapies because of multiple side-effects or because of inefficacy. Intravesical injections of botulinum toxin is a successful treatment but requires repetition of therapy every 4-6 months and exposes the patient to over dilation of the bladder (with secondary myogenic lesions of the bladder itself) and failure of the effect over time. All efforts over the last decade focused on the feasibility of a technique for control BOA and DSD avoiding rhizotomy and side effects of medical treatments. In the early 80s, Tanagho and Schmidt began implanting extradural sacral root stimulators in patients for treatment for neurogenic bladder dysfunctions. Improvement in incontinence and increase in maximal cystometric capacity have been then demonstrated in subjects with incomplete spinal cord injury but not in complete spinal cord injury. In 2002, Kirkham demonstrated that stimulation of the mixed S2 root extradurally using the Finetch-Brindley stimulator without posterior rhizotomy, has successfully suppressed BO in people with complete spinal cord injury. Stimulation with small pulse widths successfully inhibited hyperreflexive bladder contractions and increased bladder capacity, but intermittent stimulation at larger pulse widths to induce voiding was unsuccessful because of DSD between stimulation periods and less than 50% of the bladder volume was voided. Stimulation of afferent branches of the pudendal nerve has also shown to inhibit BO after complete spinal cord injury.

The feasibility of the exposure of the pudendal nerve and all further endopelveo-abdominal nerves the laparoscopic way permits us to develop new strategies of pelvic nerve stimulation as well for inhibition as for voiding the bladder.

Until now, our technique of bilateral endopelvic pudendal stimulation has been shown as the only method able to successfully control bladder hyperactivity in complete spinal cord injured people. All other techniques of implantation had failed in this indication. The blockade of bladder hyperactivity permits patients to increase bladder capacity, to reduce the amount of micturition and to control urgency incontinence (reflex incontinence).

Bladder/rectum voiding can be accomplished through interruption of pudendal stimulation. Bladder/rectum-hyperactivity-deblockade induces immediate release of autonomic hyperactivity of the bladder and of the rectum that results in bladder and/or rectum voiding.

It is well known that bladder voiding using hyperactivity alone does not permit optimal emptying of the bladder in most patients (high bladder residual) because of a concomitant detrusor-sphincter-dyssynergy (DSD=contraction of the bladder by concomitant contraction and therefore closure of the urethral sphincter). Our strategy for bladder voiding is based on deblockade of bladder hyperactivity by interruption of pudendal stimulation with concomitant muscular fatigue of the sphincter due to the pudendal stimulation during the filling phase of the bladder. Training of the muscles of the lower extremities reduces considerably the spasticity and spasms in the lower extremities because of muscles fatigue. The same effect is used for bladder voiding, pudendal stimulation during the filling phase induces a fatigue of the sphincters that is used for a successful bladder voiding after interruption of pudendal stimulation (reactivation of bladder hyperactivity which was relaxed during filling phase).

However, if DSD is too strong to permit optimal voiding of the bladder using this technique, DSD can be blocked (urethral in open status) during bladder voiding with three different kinds of pudendal stimulation, namely, high-frequency pudendus-nerve-conduction-blockade, anode blockade, and noise.

The feasibility of the "deblockade" of the bladder and rectum hyperactivity by interruption of pudendal stimulation is a major advantage of our invention comparing to all other therapies for control of bladder overactivity in spinal cord injured people. Because the dorsal rhizotomy (sacral deafferentation), medical treatments (anticholinergica, muscarinic . . . ) and intravesical botulinum toxin injections induce a permanent blockade of detrusor contractions; bladder hyperactivity can therefore not be used for bladder voiding, and patients for systematic active bladder emptying must instead use detrusor electrical stimulation (Brindley controller) or self-catheterization.

If efficiency of bladder/rectum hyperactivity is not strong enough to void the bladder empty even in combination with a sphincter blockade in opened status, pudendal blockade can be combined with sacral nerve roots and/or pelvic splanchnic nerves stimulation as described co-pending U.S. patent application Ser. No. 11/708,209, incorporated herein by reference, to increase rectum/bladder contractions and improve bladder/rectum voiding.

Reflex erections are preserved because no cutting of nerves has been done in the technique of the present invention, and as compared to the technique of sacral deafferentation. Duration and rigidity of erections is improved by selective pudendal stimulation (without any concomitant movements of the lower extremities, a classic side effect in Brindley controller).

Continuous pudendal and sciatic stimulation also permits optimal control of spasticity and spasms in the lower limbs. The continuous sciatic stimulation induces permanent isometric muscular contractions which are behind the control of spasticity and spasms, also encourages blood flow in the lower limbs by stimulation of the vegetative fibers contained in the sciatic nerves, and induces an increase of the muscle mass especially gluteal muscles mass, and both factors are essential for reduction of the risk for decubiti.

Another major advantage of the inventive strategy is that most known techniques of blockading the spasticity of the lower extremities (botox, sacral deafferentation, baclofene pump) are based on complete inhibition of movements of the lower extremities and muscle activities in the lower limbs. This in turn induces atrophy of the muscle mass that can induce deformations of articulations and bones and expose the patient for decubiti because of less tissue mass in the buttocks. The inventive technique of electrical induced isometric muscle contractions in the lower extremities constitutes an optimal training and preparation for standing and locomotion in para- and tetraplegics.

The sciatic stimulation also permits increase in the blood pressure in tetraplegics and paraplegics with lesions above to Th4 (dystonia).

Femoral stimulation induces contraction of the quadriceps and therefore extension and/or blockade in of the knees. Standing up is obtained by concomitant stimulation of the femoral nerves (knee extension) and the caudal portion of the sciatic nerves or selectively of the inferior gluteal nerves (pelvis-stability). Locomotion is obtained by stimulation of the sciatic (and branches) and femoral nerves in different chronologies that induce recovery and normal locomotion. Another safe option is to induce a blockade of the knees in extension by pudendal stimulation and concomitant stabilization of the pelvis by sciatic/gluteal stimulation that enables alternative locomotion by blockade of the knees.

Neurogenic bladder functional abnormalities in spina bifida can be classified in hyperreflexix bladder, areflexic bladder and mixed forms. Approximately 50% of children with spina bifida aperta and 25% of children with occult spinal dysraphism have a hyperactivity of the bladder which, combined with a detrusor-sphincter-dyssynergia, carries a serious risk of urinary tract damage. The incidence of renal damage is then nearly 100% in patients when not adequately treated. Therefore to prevent such irreversible damage, urological and nephrological treatments should start immediately after birth and life-long suppression of detrusor overactivity is required. Antimuscarinic therapy is the gold standard for pharmaceutical therapy; oxybutynin has proven to be inexpensive and effective and can be taken orally, intravesically, and transdermally. Repeated injection therapy of the bladder with botulinum toxin can be an alternative to antimuscarinic therapy but long-term effects have yet to be established. In failure of these therapies, patients can be treated by surgical treatments. Rhizotomies are not yet being used routinely, especially because this requires further back surgery and transsection of nerves which is sufficient for a large number of parents of such patients to reject the procedure since it is irreversible and may abolish sexual and defecation reflexes. Vesicostomy is indicated in the presence of persistent hydronephrosis and recurrent urinary tract infection when the bladder continually fails to empty. Augmentation procedures, urinary diversion and catheterizable stomas are further possible procedures to managed bladder hyperactivity and urinary incontinence, but these procedures are invasive and permanent. Control of bladder overactivity is essential in the management of spina bifida children with hyperreflexic bladders, but urinary and fecal incontinence are the major sources of poor quality of life for young people and adults with spina bifida. Social issues relating to incontinence are critical in school age children as they can interfere with educational opportunities, self esteem and social development. The teenage and young adult years are often times of poor compliance, especially with continence regimens, even more since incontinence is almost a taboo subject, viewed by many in society as a weakness and a source of shame. However, management and controlling of incontinence in spina bifida is difficult. Urological surgery for the management of incontinence is an important option for patients where other procedures, such as intermittent catheterization are insufficient or not feasible. A wide range of interventions and resources exist to assist in the successful management of urinary incontinence. Previously mentioned surgical procedures permit control of high bladder pressure and incontinence. Less invasive procedures such as transurethral injection therapy, pubovaginal sling implantation or artificial urinary sphincter implantation do also exist, but indications and efficacies depend largely on urodynamic patterns, age and sex of the patients. Achieving and maintaining bowel continence is one of the most difficult challenges for people with spina bifida. As for urinary incontinence, conservative methods and control on toileting are of major importance. When bowel emptying and fecal incontinence is not successfully controlled by conservative methods, surgical procedures may be indicated. The Malone procedure is used for management of fecal incontinence and involves bringing the appendix to the surface of the skin and creating a stoma. One disadvantage of the Malone procedure is that the appendix is unavailable to use when constructing catheterizable stomas, such as in the Mitrofanoff procedure. Caecostomy catheter is also a feasible procedure that provides a regular, predictable method for defecation but is difficult to be used long term.

Patients with spina bifida and neurogenic bladder have traditionally been managed with clean intermittent catheterization and pharmacotherapy. For patients who fail this therapy, surgical reconstruction in the form of bladder augmentation surgery using reconfigured intestine or stomach to increase the bladder capacity and reduction bladder storage pressure, are required. Despite functional success of such procedures, acceptance by parents and patients is not always easy because these surgeries are invasive, irreversible and have possible complications which are mostly irreversible. However, no technique can be said to offer reduction of bladder storage pressure and ability to volitionally void the bladder. For these reasons, alternative treatments have been sought. Sacral neuromodulation is one promising therapeutic modality, but only few series have been reported in the literature. Despite the fact that percutaneous implantation is minimally invasive and non-destructive, anatomic abnormalities and scar tissue due to previous surgeries can make implantation difficult or even impossible. In a prospective randomized controlled study to evaluate the possible benefits of sacral nerve stimulation, no significant improvement was reported in patients treated by sacral neuromodulation even if some improvement concerning bladder compliance and functional bladder capacity had been observed. Total disappearance of urinary leakage was obtained in one treated patient (1/21) but that patient still required intermittent catheterization. Improvement of transforaminal sacral nerve stimulation on bladder functions is less effective in spina bifida than in other classical indications because of partial or complete destruction of the pelvic nerves and because of limitation in the amount of nerves which can be reached by the neuromodulation since the transforaminal implantation enables stimulation from only one or at most two sacral nerves roots with one generator. To obtain the best chance for control of pelvic dysfunction especially in spina bifida, electrostimulation must reach the maximum of functional fibers involved in these functions. Therefore the best results can only be obtained by stimulation of all sacral nerve roots S2 to S4/5 or by pudendal nerve stimulation. Laparoscopy offers a minimally invasive and safe technique for implantation of electrodes, "LION procedure" referred to herein, to the sacral plexuses and/or pudendal nerves. In the special situation of spina bifida, the laparoscopic approach has the important advantage to permit a dissection of the nerves in normal anatomic conditions—without any interference with scar tissue secondary to previous surgeries—and to permit a precise morphologic and functional exploration of the nerves before final decision of implantation Control of hyperactivities, bladder and fecal retention, fecal and urinary incontinence but also voiding function can be obtained by stimulation of the pudendal nerves similarly to the technique previously described in spinal cord injured people. Even so, when spina bifida involves the nerves of standing up and locomotion, similarly to the previous described technique in paraplegics, improvement or recovery of both functions can also be obtained.

At last, the present technique is minimally invasive and reversible, avoiding any destruction or damage of the pelvic nerves, while the electrode is placed extraperitonealy in deep protection of the pelvic bone wall.

It should also be appreciated that the present detailed description of the invention is given in terms of preferred embodiments of the invention, and that various modification of steps, parts and the like would be readily apparent to a person of skill in the art, and that such modifications are considered to fall within the broad scope of the present invention.

The invention claimed is:

1. A method for altering operation of a nerve related to a given body condition, comprising the steps of:
   laparoscopically gaining access to the endopelvic area of the abdomen through the abdominal wall;
   implanting a multiple channel electrode through the access on endopelvic portions of at least one nerve of the sciatic nerve, the pudendus nerve, or both; and
   operating the electrode to electrostimulate the at least one nerve.

2. The method of claim 1, further comprising the step of visually identifying the at least one nerve through the access.

3. The method of claim 1, wherein the implanting step further comprises implanting a receiver for the electrode, and wherein the operating step comprises sending a signal to the electrode through the receiver.

4. The method of claim 1, wherein the implanting step comprises implanting the multiple channel electrode on at least two nerve roots of the at least one nerve.

5. The method of claim 1, wherein the implanting step comprises implanting the electrode on the sciatic nerve directly after fusion of the sacral nerve roots and just before the sciatic nerve enters the greater sciatic foramen.

6. The method of claim 1, wherein the implanting step comprises implanting the electrode on the pudendus nerve directly after the pudendus nerve emerges out of the sacral plexus and just before the pudendus nerve leaves the pelvis through the lesser sciatic foramen.

7. The method of claim 1, wherein the body condition is selected from the group consisting of urinary and fecal incontinence; bladder, rectum and genital hyperactivity; bladder/rectum retention; erection disfunction; pain and combinations thereof.

8. The method of claim 1, wherein the body condition is selected from the group consisting of spasticity and spasms of the lower extremities, pain, spinal cord injuries and combinations thereof.

9. The method of claim 1, wherein the body condition is a spinal cord injury, wherein the multiple channel electrode is implanted on the sciatic nerve, pudendus nerve and sacral nerve roots.

* * * * *